United States Patent
Waid et al.

(10) Patent No.: US 7,807,962 B2
(45) Date of Patent: Oct. 5, 2010

(54) BOREHOLE TESTER APPARATUS AND METHODS FOR USING NUCLEAR ELECTROMAGNETIC RADIATION TO DETERMINE FLUID PROPERTIES

(75) Inventors: Margaret Cowsar Waid, Medicine Park, OK (US); Bryan William Kasperski, Azle, TX (US); Richard C. Odom, Benbrook, TX (US); Dennis Eugene Roessler, Houston, TX (US)

(73) Assignee: Precision Energy Services, Inc., Fort Worth, TX (US)

(*) Notice: Subject to any disclaimer, the term of this patent is extended or adjusted under 35 U.S.C. 154(b) by 94 days.

(21) Appl. No.: 11/955,608

(22) Filed: Dec. 13, 2007

(65) Prior Publication Data

US 2009/0152456 A1 Jun. 18, 2009

(51) Int. Cl.
*G01V 5/08* (2006.01)
(52) U.S. Cl. .................................. 250/269.1
(58) Field of Classification Search ........... 250/269.1, 250/269.3, 254, 265, 266, 269.4, 370.1
See application file for complete search history.

(56) References Cited

U.S. PATENT DOCUMENTS

| | | | |
|---|---|---|---|
| 2,898,466 A | 8/1959 | Lintz et al. | |
| 2,961,539 A | 11/1960 | Egan | |
| 4,412,130 A | 10/1983 | Winters | |
| 5,045,692 A | 9/1991 | Arnold | |
| 5,481,105 A * | 1/1996 | Gold | 250/266 |
| 6,301,959 B1 * | 10/2001 | Hrametz et al. | 73/152.23 |
| 6,666,285 B2 * | 12/2003 | Jones et al. | 175/50 |
| 7,075,062 B2 | 7/2006 | Chen | |
| 7,507,952 B2 * | 3/2009 | Groves et al. | 250/269.1 |

FOREIGN PATENT DOCUMENTS

GB 2381862 A 5/2003

OTHER PUBLICATIONS

International Search Report-Combined Search and Examination Report from GB Patent Application 0819713.9 dated Feb. 26, 2009.

* cited by examiner

*Primary Examiner*—David P Porta
*Assistant Examiner*—Faye Boosalis
(74) *Attorney, Agent, or Firm*—Wong, Cabello, Lutsch, Rutherford & Brucculeri, L.L.P.

(57) ABSTRACT

Apparatus and methods for determining one or more fluid parameters of interest by irradiating fluid with a source of nuclear electromagnetic radiation and subsequently measuring attenuation and absorption properties of the fluid from which parameters of interest are determined. Measurements are made with a formation tester tool comprising preferably two functionally configured flow lines. The source simultaneously irradiates fluid contained in opposing irradiation sections that can be integral sections of each of the two flow lines. A radiation detector is dedicated to each irradiation section and measures radiation attenuation and absorption properties fluid contained within each flow line section. Absolute and relative fluid parameters of interest are determined from the responses of the two radiation detectors.

16 Claims, 3 Drawing Sheets

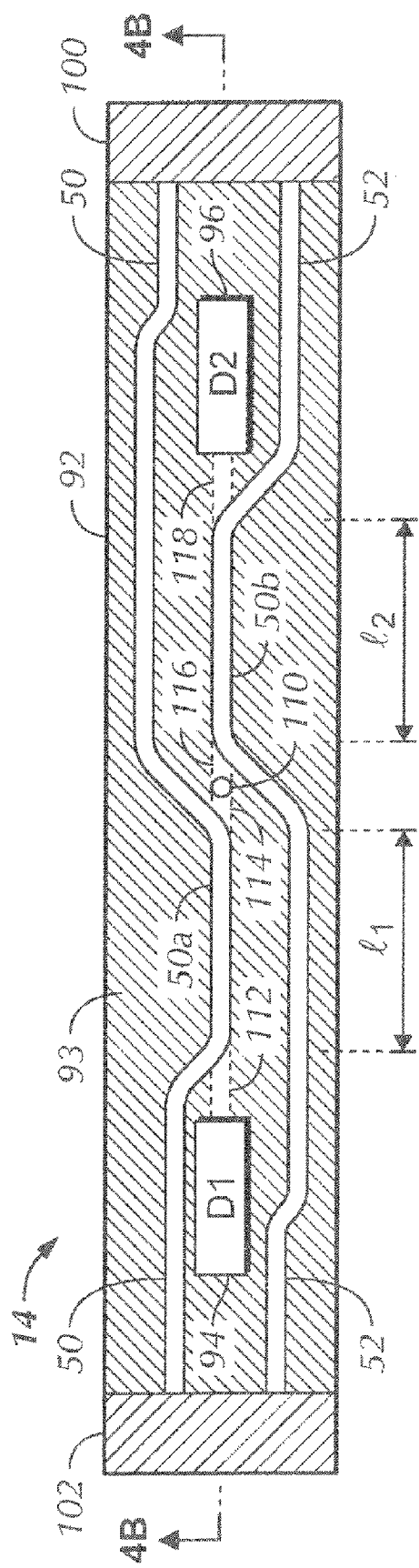
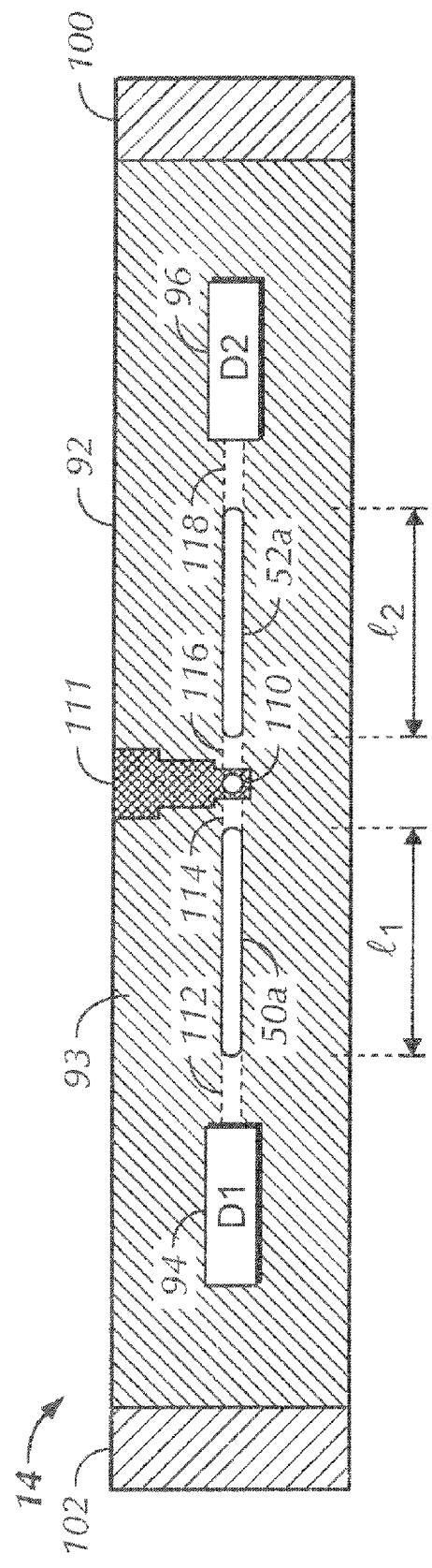

BOREHOLE TESTER APPARATUS AND METHODS FOR USING NUCLEAR ELECTROMAGNETIC RADIATION TO DETERMINE FLUID PROPERTIES

FIELD OF THE INVENTION

This invention is related to formation testing and formation fluid sampling. More particularly, the invention is related to the determination, within a borehole environment, of various properties of fluids contained therein using a downhole instrument or "tool" comprising dual, functionally configured fluid flow lines extending contiguously through various sections of the tool. The properties are determined by irradiating borehole environs fluids contained within the dual flow lines with nuclear electromagnetic radiation, and subsequently measuring attenuation and absorption of this radiation. The properties include absolute and relative measures of fluid electron density and mass density.

BACKGROUND

A variety of systems are used in borehole geophysical exploration and production operations to determine chemical and physical parameters of materials in the borehole environs. The borehole environs include materials, such as fluids or formations, in the vicinity of a borehole as well as materials, such as fluids, within the borehole. The various systems include, but are not limited to, formation testers and borehole fluid analysis systems conveyed within the borehole. In all of these systems, it is preferred to make all measurements in real-time and within instrumentation in the borehole. However, methods that collect data and fluids for later retrieval and processing are not precluded.

Formation tester systems are used in the oil and gas industry primarily to measure pressure and other reservoir parameters of a formation penetrated by a borehole, and to collect and analyze fluids from the borehole environs to determine major constituents within the fluids. Formation testing systems are also used to determine a variety of properties of formations or reservoirs in the vicinity of the borehole. These formation or reservoir properties, combined with in situ or uphole analyses of physical and chemical properties of the borehole environ fluid, can be used to predict and evaluate production prospects of reservoirs penetrated by the borehole. By definition, borehole environs fluid refers to any and all fluid, including any mixture of fluids, extracted from the formation or injected into the borehole or formation during a borehole drilling operation.

Regarding formation fluid sampling, it is of prime importance that fluid collected for analysis represents virgin formation fluid with little contamination from fluids used in the borehole drilling operation. Various techniques have been used to minimize sample contamination including the monitoring of fluid pumped through a borehole instrument or borehole "tool" of the formation tester system until one and/or more fluid properties, such as resistivity, cease to change as a function of time. Other techniques use multiple fluid input ports combined with borehole isolation elements such as packers and pad probes to minimize fluid contamination. Flowing fluid through the tool is analyzed until it has been determined that borehole fluid contamination has been minimized, at which time the fluid can be retained within the tool and typically returned to the surface of the earth for more detailed chemical and physical analyses. Regarding in situ analyses of formation fluid, it is of prime importance that fluid collected for analysis represents virgin formation fluid with little contamination from fluids used in the borehole drilling operation.

Fluid analyses typically include, but are not limited to, the determination of oil, water and gas constituents of the fluid. Technically, it is desirable to obtain multiple fluid analyses or samples as a function of depth within the borehole. Operationally, it is desirable to obtain these multiple analyses or samples during a single trip of the tool within the well borehole.

Formation tester tools can be conveyed along the borehole by a variety of means including, but not limited to, a single or multi-conductor wireline, a "slick"line, a drill string, a permanent completion string, or a string of coiled tubing. Formation tester tools may be designed for wireline usage or as part of a drill string. Tool response data and information as well as tool operational data can be transferred to and from the surface of the earth using wireline, coiled tubing and drill string telemetry systems. Alternately, tool response data and information can be stored in memory within the tool for subsequent retrieval at the surface of the earth.

Prior art formation tester tools typically comprise one dedicated fluid flow line cooperating with a dedicated pump to draw fluid into the formation tester tool for analysis, sampling, and optionally for subsequent exhausting the fluid into the borehole. As an example, a sampling pad is pressed against the wall of the borehole. A probe port or "snorkel" is extended from the center of the pad and through any mudcake to make contact with formation material. Fluid is drawn into the formation tester tool via a dedicated flow line cooperating with the snorkel. In order to isolate this fluid flow into the probe from fluid flow from the borehole or from the contaminated zone, fluid can be drawn into a guard ring surrounding the snorkel. The guard fluid is transported within the tester tool via a dedicated flow line and a dedicated pump. A more detailed description of the probe and guard ring methodology is presented in U.S. Pat. No. 6,301,959 B1, which is here entered into this disclosure by reference. This reference also discloses a dedicated flow line through which the snorkel fluid flows, and a dedicated flow line through which guard fluid flows. Fluid is sampled for subsequent retrieval at the surface of the earth, or alternately exhausted to the borehole via the dedicated flow lines and pump systems.

SUMMARY OF THE INVENTION

This disclosure is directed toward the determination of one or more fluid parameters of interest by irradiating fluid with nuclear electromagnetic radiation and subsequently measuring attenuation and absorption properties of the fluid from which parameters of interest are determined. Measurements are made with a formation tester tool comprising preferably two functionally configured flow lines which, by using one or more pumps and cooperating valves, can direct fluid to and from various axially disposed sections of the tool for analysis, sampling, and optionally ejection into the borehole or into the formation. One such section comprises a source of nuclear electromagnetic radiation such as a source gamma radiation. For purposes of disclosure, this section will be referred to as a "fluid density" section. A source of electromagnetic radiation simultaneously irradiates fluid contained in opposing irradiation sections that can be integral sections of each of the two flow lines. A radiation detector is dedicated to each of the irradiation sections and measures radiation attenuation and absorption properties fluid contained within each flow line section. Absolute and relative fluid parameters of interest are determined from the responses of the two radiation detectors.

The source of electromagnetic radiation is preferably, but not limited to, an isotopic gamma ray source such as $^{137}$Cs or $^{60}$Co. The detectors can be scintillation type such as but not limited to, sodium iodide (NaI), Yttrium Aluminum Perovskite (YAP) or bismuth germinate (BGO), or ionization type such as Geiger Muller or any other gamma ray detector. Attenuation and absorption is a function of Compton scattering, photoelectric absorption and pair production depending upon the energy of the gamma radiation traversing the fluid. Scintillation type detectors are preferred in that they can be energy biased to respond to primarily one type of detected radiation, such as Compton scatter radiation.

Absolute or relative fluid mass densities or fluid electron densities can be determined for the fluid contained within the irradiation sections. These parameters can be combined with other available information and assumptions to obtain at least an approximation of the elemental and chemical constituents of the analyzed fluids.

The formation tester system comprises a formation tester tool that is conveyed within a well borehole by a conveyance apparatus cooperating with a connecting structure. The conveyance apparatus is disposed at the surface of the earth. The connecting structure that operationally connects the formation tester tool to the conveyance apparatus is a tubular or a cable. The connecting structure can serve as a data conduit between the tool and the conveyance apparatus. The conveyance apparatus is operationally connected to surface equipment, which provides a variety of functions including processing tool response data, controlling operation of the tool, recording measurements made by the tool, tracking the position of the tool within the borehole, and the like. Measurements can be made in real-time and at a plurality of axial positions or "depths" during a single trip of the tool in the borehole. Furthermore, a plurality of measurements can be made at a single depth during a single trip of the tool in the borehole.

The formation tester tool, in the disclosed embodiment, comprises a plurality of operationally connected sections such as, but not limited to, the previously discussed fluid density section, a packer section, a probe or port section, a sample carrier section, a pump section, a hydraulics section, an electronics section, and a telemetry section. Preferably each section is controlled locally and can be operated independently of the other sections. Both the local control and the independent operation are accomplished by a section processor disposed within each tool section. Fluid flows to and from elements within a tool section, and within the functionally configured dual flow lines, are preferably controlled by the section processor. The dual fluid flow lines preferably extend contiguously through the density, packer, probe or port tool, sample carrier, and pump sections of the tool. Functions of all tool sections will be discussed in subsequent sections of this disclosure.

Fluid is preferably drawn into the tool through one or more probe or port sections using one or more pumps. Each tool section can comprise one or more intake or exhaust ports. Each intake port or exhaust can optionally be configured as a probe, guard, or borehole fluid intake port. As discussed above, borehole fluid contamination is minimized using one or more ports cooperating with borehole isolation elements such as a pad type device that is pressed against the wall of the formation, or one or more packers.

Once pumped into the tool, fluid passes through either or both of the dual flow lines simultaneously up or down through other connected sections of the tool, such as the density section. This feature gives flexibility to the configuration of the various connected tool sections. Stated another way, the axial disposition of the sections operationally connected by the functionally configured dual flow lines can be rearranged depending upon a particular borehole task.

Since two flow lines are available, multiple tasks can be performed simultaneously. As an example, samples can be collected in the sample carrier section for subsequent retrieval at the surface of the earth, while mass or electron density of fluid drawn from the probe and cooperating guard can be measured in the density section.

BRIEF DESCRIPTION OF THE DRAWINGS

The manner in which the above recited features and advantages, briefly summarized above, are obtained can be understood in detail by reference to the embodiments illustrated in the appended drawings.

FIG. 4a shows a top view of the formation fluid density section of the formation tester tool; and FIG. 4b is a side sectional view of the fluid density section.

DETAILED DESCRIPTION OF THE PREFERRED EMBODIMENTS

Figure 1:
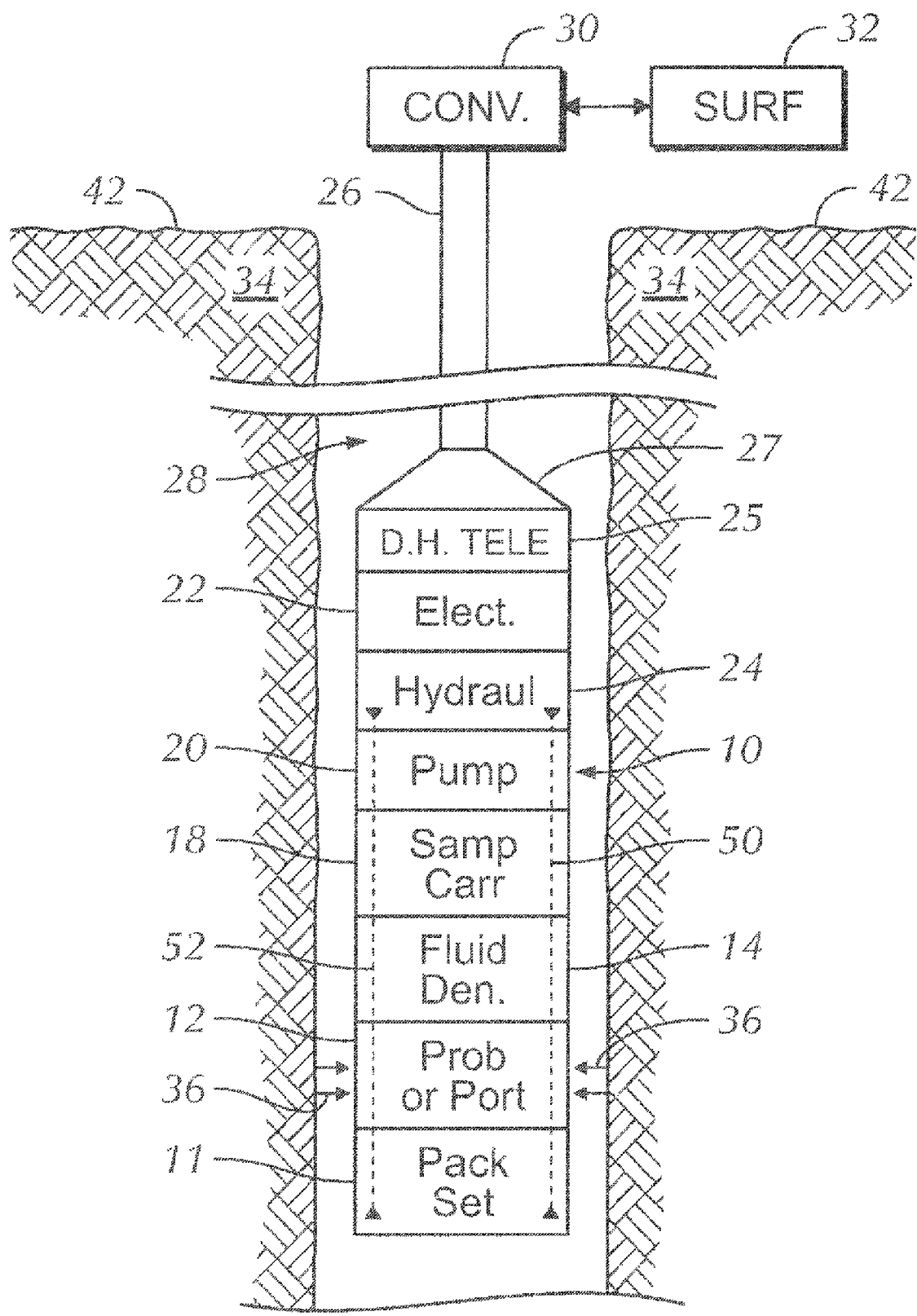
FIG. 1 illustrates conceptually the major elements of an embodiment of a formation tester system operating in a well borehole.

An overview of the dual flow line formation tester system is presented in the following paragraphs. Apparatus and methods for simultaneously measuring mass and electron density of two fluids are embodied in the fluid density section of formation tester tool.

The tester tool with functionally configurable dual flow lines is the borehole instrument component of a formation tester system. The formation fluid within the near borehole formation can be contaminated with drilling fluid typically comprising solids, fluids, and other materials. Drilling fluid contamination of fluid drawn from the formation 34 is typically minimized using one or more probes cooperating with a borehole isolation element such as a pad type device comprising a probe and a guard, as disclosed in previously referenced U.S. Pat. No. 6,301,959 B1. One or more probes extend from the pad onto the formation 34. Alternately, the connected tool sections including a packer section 11, a probe or port section 12, fluid density section 14, sample carrier section 18, a pump section 20, a hydraulics section 24, an electronics section 22, and a downhole telemetry section 25. Two fluid flow lines 50 and 52 are illustrated conceptually with broken lines and extend contiguously through the packer, probe or port tool, fluid density, sample carrier, pump, and hydraulic sections 11, 12, 14, 18, 20, and 24, respectively. One or more hydraulic flow lines (not shown) also extend continuously through the packer, probe or port tool, fluid density, sample carrier, pump, and hydraulic sections 11, 12, 14, 18, 20, and 24, respectively Again referring to FIG. 1, fluid is drawn into the tester tool 10 through a probe or port tool section 12. The probe or port section can comprise one or more intake ports. Fluid flow into the probe or port section 12 is illustrated conceptually with the arrows 36. During the borehole drilling operation, the borehole fluid and fluid within near borehole formation can be contaminated with drilling fluid typically comprising solids, fluids, and other materials. Drilling fluid contamination of fluid drawn from the formation 34 is typically minimized using one or more probes cooperating with a borehole isolation element such as a pad type device comprising a probe and a guard, as disclosed in previously referenced U.S. Pat. No. 6,301,959 B1. One or more probes extend from the pad onto the formation 34. Alternately, the formation can be isolated from the borehole by one or more packers controlled by the packer section 11. A plurality of packers can be configured axially as "straddle" packers. Straddle packers and their use are disclosed in U.S. Pat. No. 5,337,621, which is incorporated into this disclosure by reference.

With the sections of the formation tester tool 10 configured in FIG. 1, fluid passes from the probe or port section 12 through one or both functionally configurable dual flow lines 50 and 52 under the action of the pump section 20. The pump section or a plurality of pump sections cooperating with other elements of the tool, such as electrically and hydraulically operated valves, allows fluid to be transported within the dual flow lines 50 and 52 upward or downward through various tool sections. Stated another way, functionally configured flow lines cooperating with the one or more pumps and valves can also direct fluid to and from various elements within a given formation tester tool section. Manipulation of fluid flows within the formation tester as well as analysis, sampling and/or ejection operations can be varied with the formation tester disposed in the borehole using appropriate commands from the surface of the earth. A more detailed description of the operation of the dual flow lines of the formation tester tool 10 is presented in U.S. application Ser. No. 11/626,461, which is assigned to the assignee of this application and is herein entered into this application by reference.

The fluid density section 14 is used to simultaneously measure parameters such as mass density and electron density of fluid within both flow lines 50 and 52. Operation of the fluid density section is discussed in detail in subsequent sections of this disclosure.

Again referring to the tool configuration shown in FIG. 1, fluid is optionally directed via dual flow lines 50 and/or 52 to the sample carrier section 18. Fluid samples can be retained within one or more sample containers (not shown) within the sample carrier section 18 for return to the surface 42 of the earth for additional analysis. The surface 42 is typically the surface of earth formation or the surface of any water covering the earth formation.

The hydraulic section 24 depicted in FIG. 1 provides hydraulic power via one or more contiguous hydraulic flow lines (not shown) for operating numerous valves and other elements within the tool 10. Details of these hydraulic functions are presented in previously referenced U.S. application Ser. No. 11/626,461.

The Electronics section 22 shown in FIG. 1 comprises necessary tool control to operate elements of the tool 10, motor control to operate motor elements in the tool, power supplies for the various section electronic elements of the tool, power electronics, an optional telemetry for communication over a wireline to the surface, an optional memory for data storage downhole, and a tool processor for control, measurement, and communication to and from the motor control and other tool sections. Preferably the individual tool sections optionally contain electronics (not shown) for section control and measurement.

Still referring to FIG. 1, the tool 10 can have an optional additional downhole telemetry section 25 for transmitting various data measured within the tool 10 and for receiving commands from surface 42 of the earth. The downhole telemetry section 26 can also receive commands transmitted from the surface of the earth. The upper end of the tool 10 is terminated by a connector 27. The tool 10 is operationally connected to a conveyance apparatus 30 disposed at the surface 42 by means of a connecting structure 26 that is a tubular or a cable. More specifically, the lower or "borehole" end of the connecting structure 26 is operationally connected to the tool 10 through the connector 24. The upper or "surface" end of the connecting structure 26 is operationally connected to the conveyance apparatus 30. The connecting structure 26 can function as a data conduit between the tool 10 and equipment disposed at the surface 42. If the tool 10 is a logging tool element of a wireline formation tester system, the connecting structure 26 represents a preferably multi-conductor wireline logging cable and the conveyance apparatus 30 is a wireline draw works assembly comprising a winch. If the tool 10 is a component of a measurement-while-drilling or logging-while-drilling system, the connecting structure 26 is a drill string and the conveyance apparatus 30 is a rotary drilling rig. If the tool 10 is an element of a coiled tubing logging system, the connecting structure 26 is coiled tubing and the conveyance apparatus 30 is a coiled tubing injector. If the tool 10 is an element of a drill string tester system, the connecting structure 26 is again a drill string and the conveyance apparatus 30 is again a rotary drilling rig.

Again referring to FIG. 1, surface equipment 32 is operationally connected to the tool 10 through the conveyance apparatus 30 and the connecting structure 26. The surface equipment 32 comprises a surface telemetry element (not shown), which communicates with the downhole telemetry section 25. The connecting structure 26 functions as a data conduit between the downhole and surface telemetry elements. The surface unit 32 preferably comprises a surface processor that optionally performs additional processing of data measured by sensors and gauges in the tool 10. The surface processor also cooperates with a depth measure device (not shown) to track data measured by the tool 10 as a function of depth within the borehole at which it is measured. The surface equipment 32 preferably comprises recording means for recording "logs" of one or more parameters of interest as a function of time and/or depth.

It is noted that FIG. 1 illustrates one embodiment of the formation tester tool 10, and this embodiment is used to disclose apparatus and methods for making simultaneous fluid density measurements using the fluid density section 14. It should be understood, that the various tool sections including the fluid density section 14 can be arranged in different axial configurations, and multiple sections of the same type can be added or removed as required for specific borehole operations.

Basic Principles And Nomenclature

Principles of operation and nomenclature used to express mathematically the response of the dual flow tube fluid density measurements will be presented using an isotopic gamma radiation emitter (such as $^{137}Cs$ emitting monoenergetic radiation at 0.622 MeV) as a source of nuclear electromagnetic radiation. Furthermore, principles of operation and nomenclature will be presented based upon detectors such as scintillation detectors energy biased to respond essentially to radiation in the Compton scatter energy region of the energy spectrum. It should be understood, however, that the basic concepts of the invention are applicable to the emission and detection of nuclear electromagnetic radiation at other energies such as the photoelectric absorption region of the energy spectrum.

Figure 2:
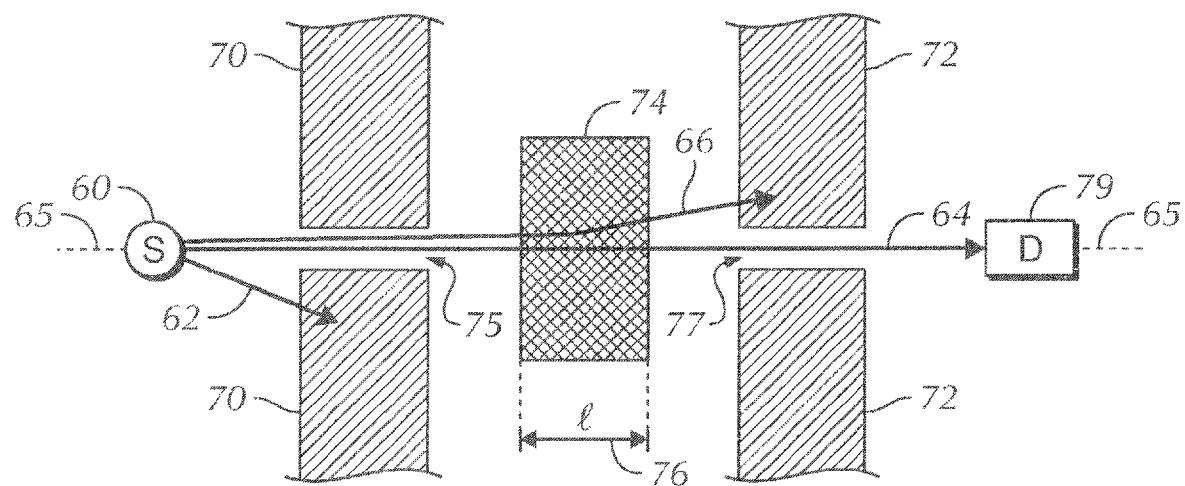
FIG. 2 depicts a source-detector-shielding arrangement for "narrow beam" gamma radiation attenuation.

FIG. 2 depicts a source-detector-shielding arrangement for "narrow beam" gamma radiation attenuation. A gamma ray source 60 is disposed to the left of a shield 70 that forms a first collimation opening 75. A gamma ray detector 70 is disposed to the right of a second shield 72 that forms a second collimation opening 77. The shielding material is a "high Z" gamma radiation attenuation and absorption material such as lead, tungsten or the like. The source 60, first collimation opening 75, second collimation opening 77 and detector 70 are on a common axis 65. A material 74 of thickness l (shown at 76) is disposed between the first and second shields 70 and 72, respectively, and intersects the axis 65. The source 60 emits gamma radiation spherically. Any emissions to the right and not essentially coincident with the axis 65 will be absorbed by the first shield 70, as illustrated conceptually by the ray path 62. Any radiation passing through the first collimation opening, entering the material 74 and undergoing coherent or incoherent scattering, will be absorbed by the second shield 72 as illustrated conceptually by the ray path 66. A portion of the emitted radiation, illustrated conceptually by the ray path 64, will pass through the first collimator opening 75, the material 74, and the second collimation opening 77 and be sensed by the detector 79.

Still referring to FIG. 2, narrow beam attenuation is expressed mathematically as $$N(E) = N_o(E) e^{-\mu(E)\rho l} = N_o(E) e^{-\sigma(E) ne \, l}$$

where

E=the energy of the gamma radiation;

N(E)=the gamma radiation flux at the position of the detector;

$N_o(E)$=the gamma radiation flux entering the material 74;

l=the path length of material traversed by gamma radiation reaching the position of the detector;

$\mu(E)$=the mass attenuation coefficient of the material 74;

$\rho(E)$=the mass density of the material 74;

$\sigma(E)$=Compton scattering cross section per electron of the material 74; and ne=the electron density of the material 74.

A more extensive discussion of equation (1) and how the terms of equation (1) can be related to fluid properties of interest can be obtained from U.S. Pat. No. 7,075,062 B2, which is herein entered into this disclosure by reference.

Figure 3:
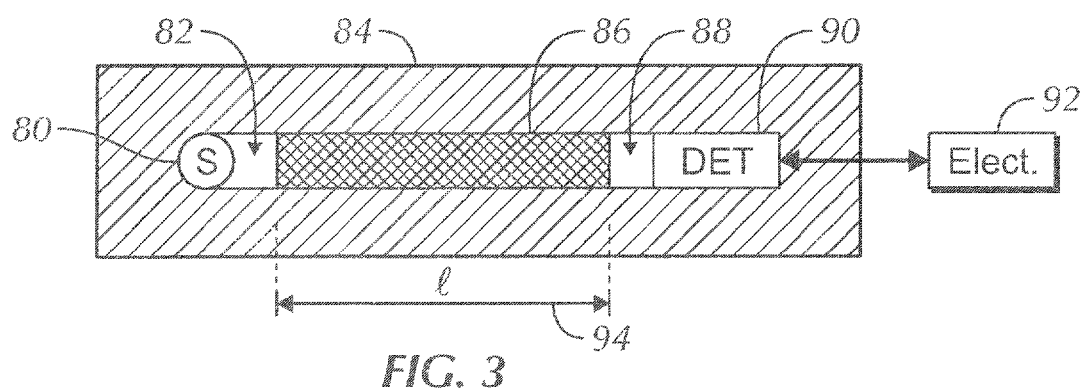
FIG. 3 illustrates a source-detector-shielding arrangement conceptually representative of a portion of the fluid density section of the formation tester tool.

FIG. 3 illustrates a source-detector-shielding arrangement conceptually representative of a portion of the fluid density section of the formation tester tool. Shielding material 84 forms a collimation opening 82 that directs gamma radiation axially through fluid 86 of axial length l shown at 94. The shielding material 84 also forms a detector collimator opening 88 so that the detector 90 responds only to gamma radiation that has axially traversed the fluid 86 along the axial path 94 of length l. The detector 90 is shown operationally connected to an electronics package 92. For a scintillation type detector, the electronics package typically would include an appropriate power supply, a preamplifier, an amplifier, and an energy biasing circuit allow the detection of gamma radiation of a predetermine energy. The response of the detector 90, typically expressed as a count rate C(E) at energy E, is $$C(E) = K C_o(E) e^{-\mu(E)\rho l} = K C_o(E) e^{-\sigma(E) ne \, l} \quad (2)$$

where $C_o(E)$=the count rate recorded with no fluid between the source and detector.

Solving equation (2) for fluid mass density yields $$\rho(E) = \mu(E) \ln[C_o(E)/C(E)]. \quad (3)$$

Solving equation (2) for fluid electron density yields $$ne = \sigma(E) \ln[C_o(E)/C(E)]. \quad (4)$$

Since $C_o(E)$ and C(E) are measured, l is known, and $\rho(E)$ and $\sigma(E)$ can be determined from other sources or by calibration, equations (3) and (4) can be used to determine fluid mass and electron density, respectively, from known or measured quantities.

The Fluid Density Tool Section

FIG. 4a shows a top view of the formation fluid density section 14 of the formation tester tool 10. The fluid section 14 comprises a source of nuclear electromagnetic radiation 110 which, for purposes of discussion, will be defined as a source of gamma radiation. Isotopic $^{137}$Cs, which emits monoenergetic gamma radiation at 0.662 MeV, is selected since this energy is well below the pair production cross section. The source 110 is collimated at 114 and 116 by shielding material 93 so that a portion of the emitted gamma radiation passes axially through preferably diametrically opposed irradiation sections 50a and 50b of lengths $l_1$ and $l_2$, respectively. In the illustration of FIG. 4a, the irradiation sections 50a and 50b are integral sections of the fluid flow tubes 50 and 52, respectively. Detector $D_1$, identified at 94, is collimated at 112 by shielding material 93 so that it is responsive only to that portion of gamma radiation axially transmitted a distance $l_1$ through fluid contained within the irradiation section 50a. Detector $D_2$, identified at 96, is collimated at 118 by shielding material 93 so that it is responsive only to that portion of gamma radiation axially transmitted a distance $l_2$ through fluid contained within the irradiation section 52a. The detectors 94 and 96 are powered and controlled by suitable electronics (not shown) so that count rates in each can be determined.

Still referring to FIG. 4a, the fluid density section 14 is terminated by connectors 102 and 100 which permit the section to be operationally connected to other sections of the formation tester tool 10. More specifically, the connectors include connectors for the fluid flow lines 50 and 52, for hydraulic flow lines (not shown) and for electrical conductors (not shown). As an example, the fluid density section 14 can be operationally connected to the probe or port section 12 (see FIG. 1) so that fluid flow tube 50 contains fluid drawn through a snorkel probe and fluid flow line 52 contains fluid drawn through a guard. Fluids contained in irradiation sections 50a and 52a would, therefore, represent fluids drawn through the probe and the guard, respectively.

FIG. 4b is a side sectional view A-A of the fluid density section 14. The source 110 is disposed in a source holder 111 that is removably inserted into the fluid density section 14 through the section wall 92. Note that the source holder is inserted and removed from the outer tool wall therefore requiring no internal disassembly of the fluid density section 14. The view shown in FIG. 4b also illustrates, from a different perspective, the irradiation sections 52a and 50a, and their locations with respect to the source 110 and to detectors 94 and 96.

Referring to both FIGS. 4a and 4b, the lengths $l_1$ and $l_2$ and of the irradiation sections 50a and 50b are preferably equal, although not required to practice the methodology of the invention. Furthermore, the major axes of the irradiation sections 50a and 50b are preferably aligned, although not required to practice the methodology of the invention. Finally, the types and energy bias settings and efficiencies of the detectors 96 and 96 are preferably equal although not required to practice the methodology of the invention.

Data Processing

General equations for fluid mass density and fluid electron density are given in equations (3) and (4), respectfully. For the embodiment of the fluid density section 14 shown in FIGS. 4a and 4b, mass densities $\rho_1$ and $\rho_2$ for fluids within irradiation sections 50a and 50b can expressed as $$\rho_1 = \mu \iota_1 \ln[C_{o,1}/C_1] \quad (5)$$

and $$\rho_2 = \mu \iota_2 \ln[C_{o,2}/C_2] \quad (6)$$

where $C_{o,1}$=the count rate recorded by detector 94 with no fluid within irradiation section 50a;

$C_1$=the count rate recorded by detector 94 with fluid within irradiation section 50a;

$C_{o,2}$=the count rate recorded by detector 96 with no fluid within irradiation section 52a; and $C_2$=the count rate recorded by detector 96 with fluid within irradiation section 52a.

The energy dependency notation (E) has been dropped assuming that the source and detectors are selected and configured to respond only to Compton scatter events.

Since the quantities $C_{o,1}$, $C_{o,2}$, $C_1$ and $C_2$ are measured, the values of $\iota_1$ and $\iota_2$ fluid density section design parameters and are known, and $\mu$ can be determined independently or by calibration using fluids of known mass density, absolute mass densities $\rho_1$ and $\rho_2$ can be determined for fluids drawn into irradiation sections 50a and 52a, respectively.

Expressions similar to equations (5) and (6) can be derived for fluid electron densities using equation (4).

It is often usefully operationally to determine relative values of mass or electron densities. More specifically it is often useful to determine only if the mass and or electron densities of fluids within the irradiation sections 50a and 52a are the same or if they are diverging in value. This determination for divergence of mass densities can be made from a combination of equations (5) and (6) which yields $$(\rho_2 - \rho_1) = \ln[C_1/C_2]/\iota\mu \quad (7)$$

where it is assumed that $\iota_1 = \iota_2 = \iota$. All terms on the right hand side of equation are measured, known or can be determined. If $\iota_2$ is not equal to $\iota_1$ and the efficiencies of the detectors 94 and 96 are not equal, then $$(\rho_2 - \rho_1) = \ln[(C_1/C_2)/(K_2/K_1)]/(F\iota_1\mu) \quad (8)$$

where $K_1$ is a multiplicative efficiency factor for detector 94, $K_2$ is a multiplicative efficiency factor for detector 96, and $F = \iota_2/\iota_1$. C1 and C2 are again measured quantified, $K_1$ and $K_2$ can be determined by calibration, and F can be computed from known design parameters $\iota_1$ and $\iota_2$.

Expressions similar to equations (7) and (8) can be derived for fluid electron densities using equation (4).

The invention is not limited to Compton scatter events. In principle, photoelectric absorption can be utilized in determining fluid parameters of interest. A lower energy source of nuclear electromagnetic radiation is preferred in a photoelectric absorption embodiment. In addition, low atomic number inserts or "low Z windows" (not shown) are required at both ends of the opposing irradiation sections 50a and 50b to allow low energy gamma radiation to enter and to exit the irradiation sections. Additional information regarding the fluids can be obtained from photoelectric absorption measurements, and by combining Compton scatter and photoelectric absorption measurements. A more detailed treatment of this methodology is presented in previously referenced U.S. Pat. No. 7,075,062 B2.

All fluid density related measurements are preferably telemetered to the surface of the earth using the previously defined telemetry of the formation tester system.

SUMMARY

The fluid density section 14 contains a source of nuclear electromagnetic radiation that is used to simultaneously irradiate fluid contained in preferably diametrically opposed irradiation sections. Shielding material forms collimator openings so that portions of the emitted radiation axially traverse each of the opposing irradiation sections. A radiation detector is dedicated to each of the irradiation sections and measures radiation attenuation and absorption properties of fluid contained within each irradiation section. Fluid parameters of interest are determined from the responses of the two radiation detectors.

The source of electromagnetic radiation is preferably an isotopic gamma ray source such as $^{137}Cs$, and the detectors are preferably scintillation type such as but not limited to, sodium iodide (Na), Yttrium Aluminum Perovskite (YAP) or bismuth germinate (BGO). The source and detector energy biases are preferably selected so that radiation attenuation and absorption is primarily a function of Compton scattering.

Absolute or relative measures of fluid mass density or fluid electron density are determined for the fluid contained in each irradiation section. These parameters can be combined with other available information and assumptions to obtain at least approximations of the elemental and chemical constituents of the analyzed fluids.

While the foregoing disclosure is directed toward the preferred embodiments of the invention, the scope of the invention is defined by the claims, which follow.

What is claimed is:

1. A fluid density section comprising:
   a source of nuclear electromagnetic radiation;
   a first irradiation section of fixed length and an opposing second irradiation section of fixed length with said source disposed there between; and
   shielding forming a plurality of collimation openings such that
   a first portion of radiation from said source is transmitted axially through said first irradiation section to a first detector, and
   a second portion of said radiation from said source is transmitted axially through said second irradiation section to a second detector.

2. A fluid density section comprising:
   a source of nuclear electromagnetic radiation;
   a first irradiation section of fixed length and an opposing second irradiation section of fixed length with said source disposed there between; and
   shielding forming a plurality of collimation openings such that
   a first portion of radiation from said source is transmitted axially through said first irradiation section to a first detector, and
   a second portion of said radiation from said source is transmitted axially through said second irradiation section to a second detector; wherein
   said first irradiation section and said second irradiation section are operationally connected to a port or probe section of a formation tester tool via dual flow lines.

3. The fluid density section of claim 2 wherein major axes of said first and said second irradiation sections are aligned.

4. The fluid density section of claim 2 wherein said source of nuclear electromagnetic radiation comprised an isotopic gamma radiation emitter.

5. The fluid density section of claim 4 wherein said first portion and said second portion of said radiation from said source is attenuated by Compton scattering.

6. The fluid density section of claim 2 wherein a property of fluids contained within said first and said second irradiation sections is determined from the respective responses of said first detector and said second detector.

7. The fluid density section of claim 6 wherein a relative property of fluids contained within said first and said second radiation sections is determined by combining said responses of said first and said second detectors.

8. The fluid density section of claim 6 wherein said property is fluid mass density or fluid electron density.

9. A method for measuring a property of a fluid, the method comprising:
   providing a source of nuclear electromagnetic radiation;
   disposing said source between a first irradiation section of fixed length and an opposing second irradiation section of fixed length; and
   providing shielding to form a plurality of collimation openings such that
      a first portion of radiation from said source is transmitted axially through said first irradiation section to a first detector, and
      a second portion of said radiation from said source is transmitted axially through said second irradiation section to a second detector.

10. A method for measuring a property of a fluid, the method comprising:
   providing a source of nuclear electromagnetic radiation;
   disposing said source between a first irradiation section of fixed length and an opposing second irradiation section of fixed length; and
   providing shielding to form a plurality of collimation openings such that
      a first portion of radiation from said source is transmitted axially through said first irradiation section to a first detector, and
      a second portion of said radiation from said source is transmitted axially through said second irradiation section to a second detector; and
   operationally connecting said first irradiation section and said second irradiation section to a port or probe section of a formation tester tool via dual flow lines.

11. The method of claim 10 further comprising aligning major axes of said first and said second irradiation sections.

12. The method of claim 10 wherein said source of nuclear electromagnetic radiation comprised an isotopic gamma radiation emitter.

13. The method of claim 12 wherein said first portion and said second portion of said radiation from said source is attenuated by Compton scattering.

14. The method of claim 10 further comprising determining a property of fluids contained within said first and said second irradiation sections from the respective responses of said first detector and said second detector.

15. The method of claim 14 further comprising determining a relative property of fluids contained within said first and said second radiation sections by combining said responses of said first and said second detectors.

16. The method of claim 14 wherein said property is fluid mass density or fluid electron density or fluid mass density and fluid electron density.

* * * * *